United States Patent [19]

Marx et al.

[11] Patent Number: 4,759,872

[45] Date of Patent: Jul. 26, 1988

[54] WOOD PRESERVATIVES

[75] Inventors: Hans-Norbert Marx, Buehl-Weitenung; Reimer Goettsche, Baden-Baden; Wendelin Hettler, Sinzheim-Muellhofen, all of Fed. Rep. of Germany

[73] Assignee: Dr. Wolman GmbH, Sinzheim, Fed. Rep. of Germany

[21] Appl. No.: 28,578

[22] Filed: Mar. 20, 1987

[30] Foreign Application Priority Data

Mar. 21, 1986 [DE]  Fed. Rep. of Germany ....... 3609544

[51] Int. Cl.$^4$ ...................... C09K 15/32; C09K 15/18; A01N 59/20; A61K 33/34

[52] U.S. Cl. ............................ 252/400.53; 106/15.05; 106/18.3; 106/18.32; 252/400.4; 252/400.41; 252/401; 252/405; 252/407; 252/607; 423/42; 424/140; 424/141; 424/148; 424/150; 424/166; 424/DIG. 11; 427/377; 427/396; 427/397

[58] Field of Search ................... 252/607, 601, 389.53, 252/400.53, 400.4, 401, 405, 407, 400.41; 106/15.05, 18.3, 18.31, 18.32; 424/140, 141, 143, DIG. 11, 148, 129, 150, 166; 423/42, 43, 44; 427/314–317, 372.2, 377, 394, 396, 397

[56] References Cited

U.S. PATENT DOCUMENTS

| | | | |
|---|---|---|---|
| Re. 31,576 | 5/1984 | Hilditch | 424/141 |
| 2,554,319 | 5/1951 | Ayers | 424/140 |
| 2,850,405 | 9/1958 | Bottoms | 424/140 |
| 3,007,844 | 11/1961 | Schulz | 424/140 |
| 3,681,492 | 8/1972 | Kotzbauer | 424/141 |
| 3,945,835 | 3/1976 | Clarke et al. | 424/141 |
| 4,047,940 | 9/1977 | Rappas et al. | 423/42 |
| 4,080,430 | 3/1978 | Shah et al. | 423/274 |
| 4,193,993 | 3/1980 | Hilditch | 424/141 |
| 4,649,065 | 3/1987 | Hein et al. | 428/541 |
| 4,654,380 | 3/1987 | Makepeace | 523/122 |
| 4,656,060 | 4/1987 | Krzyzewski | 427/397 |

OTHER PUBLICATIONS

Hawley, G. 1981, The Condensed Chemical Dictionary, 10th edition, Van Nostrand Reinhold Company, New York, p. 292.

*Primary Examiner*—Stephen J. Lechert, Jr.
*Assistant Examiner*—Howard J. Locker
*Attorney, Agent, or Firm*—Oblon, Fisher, Spivak, McClelland & Maier

[57] ABSTRACT

A wood preservative contains a water-soluble, alkaline copper(II) complex and a water-soluble thiocyanate or iodide and may contain a reducing agent.

4 Claims, No Drawings

WOOD PRESERVATIVES

The present invention relates to a wood preservative in the form of an aqueous solution of a copper (II) compound which is converted to a copper (I) compound in the wood.

Wood preservatives based on inorganic copper compounds with alkanolamines as complex formers are known (European Pat. No. 89,958). They have the disadvantage that, after being fixed in the wood, about 10% of the copper are washed out. In the case of the abovementioned wood preservatives whose solutions have a pH greater than 8, fixing of copper in the wood takes place from a pH of about 7.5–8.0, basic compounds, e.g. copper hydroxide, being formed. These copper compounds are insoluble down to a pH of about 5.0 but can be dissolved below this value by dilute acids, as present in acidic soils or acid rain, so that a greater amount of copper is washed out from the wood under these conditions.

The use of other complex formers for the copper, such as polyamines, e.g. dipropylenetriamine, has the disadvantage that 40% of Cu or more may be washed out. The same applies to the use of hydroxycarboxylic acids at a pH above 6, e.g. tartaric acid. In some cases, this results in washing out being increased to above 50%.

If wood is impregnated with the abovementioned preservative, i.e. with a copper compound complexed with an amine or ammonia, impregnation imparts a greenish color to the wood, and this color may produce color effects in subsequent decorative, transparent coats.

We have found that the abovementioned disadvantages are overcome if copper(II) compounds are complexed with ammonia, amines, organic hydroxycarboxylic acids or mixtures of these in aqueous solution at a pH above 6 and the complexes are converted in the wood, by reduction, to sparingly soluble, stable, weather-resistant copper(I) compounds which are difficult to Leach, in particular copper(I) oxide, copper(I) thiocyanate or copper(I) iodide.

For example water-soluble thiocyanates or iodiodes, such as alkali metal, amine or ammonium thiocyanates or the corresponding iodides or a mixture of the compounds, are added to the aqueous solutions of the copper(II) complexes. After impregnation of the wood with the novel preservatives, the copper(II) compound is gradually reduced in the presence of the thiocyanates or iodides by wood constituents or, where relevant, added reducing agents, in particular glucose, and copper(I) thiocyanate or iodide is formed. This is evident from the color of the small wood blocks which lose their bluish-green color gradually during the fixing process and finally show virtually no discoloration. This process can be substantially accelerated by supplying energy, for example super-heated steam. The blocks lose their initial color or gradually become browish-yellow, this color being an indication of the presence of red copper(I) oxide in the wood. It is formed in particular where thiocyanate is present in less than the stoichiometric amount and an additional reducing agent, e.g. glucose, is present. The abovementioned reduction of copper(II) to copper(I) is accompanied by a substantial reduction in the amount of copper washed out from the wood when water acts on the impregnated wood.

It is advisable to add thiocyanate or iodide in an amount such that the conversion to the copper(I) compounds can take place stoichiometrically. However, the amount used may be in excess of, or less than, the stoichiometric amount, for example by up to 10%. In the subsequent accelerated fixing, for example by means of super-heated steam, it is not necessary to use a stoichiometric amount of thiocyanate or iodide; for example, when thiocyanate was present in an amount which was up to about 50% less than the stoichiometric amount, there was virtually no increase in the amount of copper washed out. This applies in particular when additional reducing agent, e.g. glucose, are added to the impregnating solution. In addition to the copper(I) thiocyanate formed, the remaining copper is reduced to copper(I) oxide.

The amount of thiocyanate or iodide added is, for example, from 5 to 35%, preferably from 10 to 30%, in particular from 14 to 28%.

Water-soluble or insoluble organic or inorganic copper(II) compounds may be used for the wood preservatives, the said compound being dissolved in water at a pH of from 6 to 11, depending on the complex former used.

In this case, the known complex formers are used in an amount which is sufficient for complex formation (1 g atom of copper generally requires, for example, 4 mol equivalents of amine or ammonia) and, if necessary, also brings the impregnating solution to the desired pH.

It is also possible to use mixtures of amines, ammonia and hydroxycarboxylic acids and/or their salts for complexing. Examples of suitable hydroxycarboxylic acids are lactic acid, tartaric acid, citric acid and malic acid, examples of suitable amines are alkanolamines, such as ethanolamine, isopropanolamine, 1,1- and 1,2-diaminoethanol, aminoethylethanolamine, diethanolamine or dimethylethanolamine, polyamines, e.g. dipropylenetriamine, and alkylamines, e.g. triethylamine, and mixtures of the various amines.

The pH of the wood preservatives and of the impregnating solutions can be established by adding an alkali, ammonia or a water-soluble amine, if necessary independently of complex formation.

Suitable concentrates contain, for example,
from 5 to 50% of Cu(II) compounds,
from 15 to 50% of complex formers,
from 5 to 30% of thiocyanate or iodide or a mixture of these,
from 0 to 30% of a compound having a fungicidal anion and
from 0 to 30% of a reducing agent, e.g. glucose,
the percentages being percentages by weight in each case and summing to 100, and, if required, water. However, the invention also embraces the impregnating solutions which have appropriately lower specific concentrations and can be prepared by dilution with water.

The novel wood preservatives can, if required, contain additional conventional components, such as corrosion inhibitors, e.g. isononanoic acid or its salts.

It is advisable to add compounds containing a fungicidal anion, e.g. boric acid, borates, fluorides or fluoborates or mixtures of these, in order that regions of the wood (heartwood) which are not accessible to impregnation can also be impregnated by means of these components capable of diffusion.

The novel concentrates may be in the form of more or less viscous liquids, in the form of pastes or in solid form.

For accelerated fixing, in addition to the use of superheated steam, it is also possible to supply the necessary energy by, for example, exposing the impregnated wood to a high frequency field.

The Example which follows illustrates the invention.

EXPERIMENTAL PROCEDURE

In each case, 20 standard pine sapwood blocks (5×15×50 mm) were impregnated with an aqueous solution of the novel preservatives. 10 blocks were stored in glass containers to permit fixing and were washed out with water after 4 weeks. The other 10 blocks were treated with steam at 100° C. 2 hours after impregnation, until the blocks reached a temperature of not less than 90° C. This took 2 hours. The blocks treated in this manner were then immediately washed out with water.

The eluates from this washout procedure were collected separately, and the amount of copper in them was determined. The amount of copper washed out was expressed in each case as a ratio of the Cu content of the blocks. Percentages are by weight.

EXAMPLE 1

|  | a - no additive | b - with thiocyanate | c - with iodide |
|---|---|---|---|
| $Cu(OH)_2CuCO_3$ | 12.10% | 12.10% | 12.10% |
| tartaric acid | 33.00% | 33.00% | 33.00% |
| NaOH | 19.20% | 19.20% | 19.20% |
| water | 35.70% | 19.00% | 19.00% |
| KSCN | — | 16.70% | — |
| KI | — | — | 16.70% |

60 g of the solution were mixed with 1 liter of water, ie. the use concentration was 6%.

| Washing out of Cu | | | |
|---|---|---|---|
| Standard fixation (storage for 4 weeks) | 60.50% | 1.50% | 17.50% |
| Accelerated fixation (with superheated steam) | 20.20% | 18.50% | 16.50% |
| amount of condensate(*) | 51.20% | 0.30% | 15.50% |

(*)During the heating up period at the beginning of a treatment with superheated steam, when fixation is not yet complete, condensate being formed may wash out some of the preservative from the blocks. This amount was not included in the calculation of the amount washed out.

Because of the surface/volume ratio of the blocks as well as their small volume, washing out as a result of condensate formation is greater than in the case of roundwood or cutwood, where there is less superficial washing out through condensate formation, the ratio for roundwood to blocks being from 1:3 to 1:5.

EXAMPLE 2

|  | no additive | with thiocyanate | |
|---|---|---|---|
| $Cu(OH)_2.CuCO_3$ | 14.50% | 14.50% | 14.50% |
| tartaric acid | 14.50% | 14.50% | 14.50% |
| monoethanolamine | 30.50% | 30.50% | 30.50% |
| boric acid $H_3BO_3$ | 4.00% | 4.00% | 4.00% |
| KSCN | — | 27.50% | — |
| $NH_4SCN$ | — | — | 27.50% |
| water | 36.50% | 9.00% | 9.00% |

Use concentration: 5%

| Washing out | | | |
|---|---|---|---|
| Normal fixation | 28.10% | 2.20% | 2.00% |
| Accelerated fixation | 15.70% | 13.60% | 7.00% |
| Amount of condensate | 20.10% | 0.50% | 0.30% |

EXAMPLE 3

|  | no additive | with thiocyanate |
|---|---|---|
| $Cu(OH)_2.CuCO_3$ | 15.00% | 15.00% |
| lactic acid | 15.00% | 15.00% |
| boric acid $H_3BO_3$ | 4.00% | 4.00% |
| monoethanolamine | 31.00% | 31.00% |
| $NH_4SCN$ | — | 15.00% |
| water | 35.00% | 20.00% |

Use concentration: 5%

| Washing out | | |
|---|---|---|
| Normal fixation | 11.10% | 2.80% |
| Accelerated fixation | 13.80% | 9.50% |
| Amount of condensate | 8.10% | 0.60% |

EXAMPLE 4

|  | no additive | with thiocyanate | with iodide |
|---|---|---|---|
| $Cu(OH)_2.CuCO_3$ | 20.00% | 20.00% | 20.00% |
| monoethanolamine | 40.00% | 40.00% | 40.00% |
| boric acid $H_3BO_3$ | 5.00% | 5.00% | 5.00% |
| $NH_4SCN$ | — | — | 20.00% |
| KI | — | — | 20.00% |
| water | 35.00% | 15.00% | 15.00% |

Use concentration: 4%

| Washing out | | | |
|---|---|---|---|
| Normal fixation | 9.10% | 1.60% | 2.30% |
| Accelerated fixation | 8.50% | 6.20% | 9.50% |
| Amount of condensate | 8.90% | 0.50% | 1.20% |

EXAMPLE 5

|  | no additive | with thiocyanate |
|---|---|---|
| $Cu(OH)_2.CuCO_3$ | 15.00% | 15.00% |
| dipropylenetriamine | 28.00% | 28.00% |
| oxalic acid | 17.50% | 17.50% |
| boric acid $H_3BO_3$ | 4.00% | 4.00% |
| $NH_4SCN$ | — | 15.00% |
| water | 35.50% | 20.50% |

Use concentration: 5%

| Washing out | | |
|---|---|---|
| Normal fixation | 45.70% | 12.50% |
| Accelerated fixation | 15.20% | 17.50% |
| Amount of condensate | 41.00% | 8.90% |

EXAMPLE 6

|  | no additive | with thiocyanate |
|---|---|---|
| commercial dilute ammoniacal copper borate solution Cu content 4.1% B content 1.10% | 100 parts | 100 parts |
| $NH_4SCN$ | — | 5 parts |

Use concentration: 10%

| Washing out | | |
|---|---|---|
| Normal fixation | 15.10% | 4.20% |
| Accelerated fixation | 8.00% | 6.50% |
| Amount of condensate | 18.60% | 0.60% |

EXAMPLE 7

15% of $Cu(OH)_2.CuCO_3$
30% of monoethanolamine
5% of $H_3BO_3$
20% of D-glucose -continued

| 7.5% of NH4SCN Use concentration: 5% | |
| --- | --- |
| Washing out | |
| Accelerated fixation | 8.9% |
| Amount of condensate | 0.7%. |

We claim:

1. A wood preservative based on a copper(II) compound in the form of a complex with ammonia, an amine, an organic hydroxycarboxylic acid or a mixture of these compounds, which is soluble in water at a pH above 6, wherein the preservative contains a compound having an anion selected from the group consisting of a thiocyanate, an iodide and mixtures thereof which converts the copper in the wood into a stable copper(I) compound.

2. A wood preservative as claimed in claim 1, which additionally contains a further reducing agent.

3. A method of preserving wood by impregnation with a wood preservative as claimed in claim 1, wherein energy is applied to the wood during or after impregnation.

4. A method as claimed in claim 3, wherein the energy is applied to the wood in the form of superheated steam.

* * * * *